(12) United States Patent
Kleinert et al.

(10) Patent No.: US 8,673,027 B2
(45) Date of Patent: Mar. 18, 2014

(54) ONE-STEP CONVERSION OF SOLID LIGNIN TO LIQUID PRODUCTS

(75) Inventors: Mike Kleinert, Berlin (DE); Tatjana (Tanja) Barth, Bergen (NO)

(73) Assignee: Bergen Teknologioverforing AS, Bergen (NO)

( * ) Notice: Subject to any disclaimer, the term of this patent is extended or adjusted under 35 U.S.C. 154(b) by 527 days.

(21) Appl. No.: 12/673,242

(22) PCT Filed: Aug. 13, 2008

(86) PCT No.: PCT/EP2008/006672
§ 371 (c)(1),
(2), (4) Date: Apr. 1, 2011

(87) PCT Pub. No.: WO2009/021733
PCT Pub. Date: Feb. 19, 2009

(65) Prior Publication Data
US 2011/0173875 A1    Jul. 21, 2011

(30) Foreign Application Priority Data
Aug. 14, 2007  (EP) .................................... 07015978

(51) Int. Cl.
| | |
|---|---|
| C10L 1/00 | (2006.01) |
| C07C 37/00 | (2006.01) |
| C08G 61/00 | (2006.01) |
| C10L 1/10 | (2006.01) |
| C07C 37/54 | (2006.01) |
| C07C 39/06 | (2006.01) |

(52) U.S. Cl.
CPC ............... *C08G 61/00* (2013.01); *C07C 37/00* (2013.01); *C10L 1/10* (2013.01); *C10G 2300/1014* (2013.01); *C10G 2300/4025* (2013.01); *C10G 2300/4006* (2013.01); *C10G 2300/4012* (2013.01); *C07C 37/004* (2013.01); *C07C 37/54* (2013.01); *C07C 39/06* (2013.01)
USPC ................................ 44/300; 568/716; 528/86

(58) Field of Classification Search
USPC ................................ 44/300; 528/86; 568/716
See application file for complete search history.

(56) References Cited

U.S. PATENT DOCUMENTS

| | | |
|---|---|---|
| 3,186,923 A | 6/1965 | Warren |
| 3,976,437 A | 8/1976 | Shang et al. |
| 5,196,069 A | 3/1993 | Cullingford et al. |

FOREIGN PATENT DOCUMENTS

| | | | |
|---|---|---|---|
| AU | 4979679 | * | 2/1981 |
| AU | 518 450 B2 | | 10/1981 |
| CN | 1566289 A | | 1/2005 |
| EP | 0 204 354 A1 | | 12/1986 |
| FR | 2 770 543 A | | 5/1999 |
| WO | 0044699 A | | 8/2000 |
| WO | WO0044699 | * | 8/2000 |
| WO | WO2007111605 | * | 10/2007 |

OTHER PUBLICATIONS

Yu et al.,"Kinetics, Catalysis, and Reaction Engineering", Ind. Eng. Chem. Res., 1998, 37, pp. 2-10.
Chinese Office Action for corresponding Chinese Application No. 200880106910.0 dated Nov. 19, 2012, 18 pages.

* cited by examiner

*Primary Examiner* — Prem C Singh
*Assistant Examiner* — Chantel Graham
(74) *Attorney, Agent, or Firm* — Rothwell, Figg, Ernst & Manbeck, PC

(57) ABSTRACT

The present invention refers to a method of converting a lignin material into a liquid product and the liquid product obtainable by the method.

38 Claims, 4 Drawing Sheets

ONE-STEP CONVERSION OF SOLID LIGNIN TO LIQUID PRODUCTS

CROSS REFERENCE TO RELATED APPLICATION

This application is a 35 U.S.C. 371 National Phase Entry Application from PCT/EP2008/006672, filed Aug. 13, 2008, which claims the benefit of European Patent Application No. 07015978.5 filed on Aug. 14, 2007, the disclosure of which is incorporated herein in its entirety by reference.

The present invention refers to a method of converting a lignin material into a liquid product and the liquid product obtainable by the method.

Use of biomass for energy purposes is increasingly a focus both in research and development of alternative energy sources. The need for exploiting energy resources that are renewable, globally available and do not contribute to adverse climate effects is generally accepted (1), but the specific solutions are still in a process of development, and the list of options is still open—and expanding.

Producing renewable liquid fuels that are suitable for use in motor vehicles is perhaps the greatest challenge in the biofuel area. The quickest route to general use would be to produce a fuel that is compatible with the existing motor technology and infrastructure, which would make it faster and simpler to implement than fuels like hydrogen and electricity that require major changes at several levels of technology. Ethanol, biodiesel (FAMEs) and biogas are obvious examples of such fuels, but the amounts produced based on present day resources and technology will only cover a fraction of the total needed on a global basis (2).

For the production of renewable motor fuels (3), woody biomass is in many perspectives the preferred raw material. Natural wood is a large resource in many areas of the world and increased exploitation is sustainable. In addition, short rotation forestry may increase the available resources without competing with food production (4), thus reducing negative side-effects of change in land use or intense farming of e.g. soya, corn or sugar cane.

Ethanol production from the carbohydrate fractions of wood is already close to commercial application. However, the wood raw material also contains other components: The average composition of a Norwegian Norway spruce (*Picea abies*) log is 41% cellulose, 28% hemicellulose, 27% lignin and 4% resins. Thus, the use of the carbohydrate fractions leaves around one third of the material as a low-value by-product or waste. This is a significant drawback for the economy of the whole process.

For optimal use of the renewable resources it is preferable to think in terms of a bio-refinery (5,6), where the raw material coming into the refinery is completely transformed to a range of products. The product slate can then be designed to give the best possible total economy. Within this concept, the lignin and extractives that are "left over" after ethanol production should be processed to give value-added products, rather than just being burned as a process energy source. Even the 4% resins in the raw material can give a significant contribution to the total product slate if good products are obtained. In a more global context lignin, right after cellulose, has to be considered as second most prominent and abundant source of renewable and sustainable carbon.

U.S. Pat. No. 3,186,923 discloses a method of increasing the yield of valuable, low-molecular weight pyrolysate products having a high oxygen content such as guaiacol, vanillin and catechol by pyrolizing natural vegetable materials such as bark, woodwaste and lignins. Pyrolysis takes place in a reactor tube, wherein commensurated bark is charged and formic acid is fed as a liquid. The reaction mixture is heated up to 450° C. while flushing it with nitrogen. The process takes place at reduced atmospheric pressures of 20 to 100 mmHg.

AU B1 49 796/79 describes a method for hydrolising lignocellulosic material with formic acid in the presence of water at temperatures of 60-70° C., and ambient pressure thereby converting hemicellulose to its hydrolysis product, converting cellulose to glucose and dissolving a major portion of the lignin content. In the following, the solid residue is reacted with formic acid and hydrochloric acid thereby converting residual cellulose to glucose and converting other polysaccharides to monosaccharides. Remaining lignin residues are collected after the last step and are discarded.

FR 2 770 543 describes a method for producing cellulose, lignin, sugar and acetic acid from bark cellulose as the starting material. The starting material is mixed with formic acid and acetic acid and then heated to 50° C. at ambient pressure. A solid fraction, which mainly contains cellulose, is separated from the organic phase, which mainly consists of formic acid, acetic acid, monomeric sugars, solubilized polymers and lignins. The lignin fraction is not further worked up.

In this work, we have focussed on the conversion of lignin to liquids by pyrolysis/solvolysis, with the aim of obtaining liquid fuels also from this part of the raw material. The initial aim is to produce organic liquids (oils) that are compatible with petroleum products, and thus can be used as blending components in existing motor fuels. For this purpose we have selected closed system pyrolysis in a liquid reaction medium as the thermochemical conversion method, since the high oxygen content and the dominance of aromatic structures in lignins require considerable chemical transformation to give stable, petroleum-soluble liquid products. Simple classical pyrolysis technologies that only apply heating will result in conversion mainly to solid coke, just as lignin-rich material in nature would be transformed into coal, not petroleum, during natural conversion processes (7,8). The more popular processes of fast or flash pyrolysis, regardless of the applied method of heating, is primarily aimed at producing liquids. However, these bio-oils or bio-crude oils are, like the biomass they are derived from, very rich in oxygen and therefore polar and are often chemically not stable over time (9). Coke formation is expected to be higher when lignin is the raw material compared to whole wood, so the fast pyrolysis technology is overall not considered the optimal technology for thermochemical conversion in this case.

The vast majority of lignin research in terms of transportation fuel production is done on hydrodeoxygenation or zeolite upgrading that utilise gaseous hydrogen and different catalysts to remove the covalently bound oxygen as water (10). Recent research has e.g. lead to patents for a "Process for catalytic conversion of lignin to liquid bio-fuels" (11). These techniques involve a two or three step procedure in which first the natural polymer is depolymerised by strong bases at elevated temperatures and subsequently the respective mono- or oligomers are hydrotreated in the presence of heavy and/or transition metals and their oxides. The products consist of alkyl phenols or alkylbenzes respectively, the former known to possess distinct octane-increasing properties.

Further, a method is known (12) for producing liquid hydrocarbons by thermomechanic cracking and hydrogenating a solid starting material, wherein the solid starting material and a hydrogen donor-solvent system are reacted under conditions of non-stationary flow in a reaction rotor device with flow modulation. The hydrogen donor-solvent system consists of water and a mixture of hydrocarbon fractions with boiling temperatures in the range of 35-100° C. with a circulating-postfractionating residue having a boiling temperature in the range of 450-600° C. and a solidification temperature of 20° C.

An object of the present invention was to provide a method of converting a lignin material into a liquid product wherein the disadvantages associated with the prior art are at least partially overcome.

Generally, the present invention refers to a liquefaction process that is capable of depolymerising the natural biopolymer lignin into a liquid product that has significantly reduced oxygen content and is therefore suitable as blending component of conventional fossil fuels in auto-motive applications. During the conversion depolymerisation and oxygen removal by formation of water takes place in a single operation, which is a major novelty as compared to presently known multi-step process yielding liquid products of comparable quality.

Preferably, the method of the invention comprises a slow pyrolysis or solvolysis process that converts a two-phase system of a liquid reaction medium and of solid lignin, which stems from e.g. ethanol production from lignocellulosic biomass (wood) or waste streams from pulp and paper industry, both biomass streams in which the desired carbohydrate fraction like cellulose etc. is removed, into another two-phase system comprising a liquid aqueous phase and a liquid bio-oil (product) phase. The phases can easily be separated. No or very little solid by-product (char) is formed, which, however, is always the case in presently known slow pyrolysis processes. Yields of product oils are preferably about at least 90% or higher on a mass basis from solid lignin to liquid bio-oil.

The amount of covalently bound oxygen in the liquid product is significantly reduced, making the liquid product highly compatible with fossil fuels.

Preferably, in the invention heating rates in the range of 1-30° C./min, preferably 1-20° C./min and residence times of a couple minutes to some hours are used.

A flow sheet of basic process steps for a preferred embodiment of the invention is shown in FIG. 1.

Accordingly, the present invention provides a method of converting a lignin material into a liquid product, comprising the steps:
(a) providing a lignin starting material,
(b) subjecting said starting material to a treatment in a reaction medium under elevated pressure comprising:
   (i) at least one $C_1$-$C_2$ carboxylic acid, and/or salts and/or esters thereof,
   (ii) optionally at least one alcohol and/or water,
   (iii) optionally an alkylating agent, and
   (iv) optionally an inorganic salt,
   wherein said starting material is converted to a liquid product, and
(c) obtaining the liquid product from the reaction medium.

As used herein, "lignin" and "lignin material" are used interchangeably and refer to a biomass material which is an amorphous three-dimensional energy-rich phenolic biopolymer. Lignin is typically deposited in nearly all vascular plants and provides rigidity and strength to their cell walls. The lignin polymeric structure is composed primarily of three phenylpropanoid building units interconnected by etheric and carbon-to-carbon linkages. Non-limiting examples of lignin material can include agricultural lignin, wood lignin, lignin derived from municipal wast, Kraft lignin, organosolve lignin, and combinations thereof. Preferably, the solid lignin starting material is selected from wood lignin or products derived therfrom such as processed steam explosion material, hydrolysis lignin or lignosulfonate from pulp and paper industries and combinations thereof. Examples of lignins which may be used in the present invention are shown in Table 1.

TABLE 1

Lignin starting materials and their chemical composition.

| Different industrial or scientific lignin samples | C [%] | H [%] | O [%] | H/C mol. | H/O mol. | C/O mol. |
|---|---|---|---|---|---|---|
| Organosolv (commercial) | 65 | 5.7 | 28.7 | 1.04 | 3.15 | 3.02 |
| Hydrolytic (commercial) | 63 | 5.7 | 30 | 1.08 | 3.02 | 2.80 |
| Alkali (commercial) | 59 | 5.6 | 33.5 | 1.13 | 2.65 | 2.35 |
| milled wood lignin | 58 | 5.1 | 36.2 | 1.05 | 2.24 | 2.13 |
| Organosolv (commercial, Aldrich) | 66.3 | 5.3 | 27.9 | 0.95 | 3.02 | 3.17 |
| DP510 (commercial, Borregaard) | 42.0 | 4.6 | 47.1 | 1.31 | 1.55 | 1.19 |
| DP511, dry (Borregaard) | 47.6 | 4.3 | 47.2 | 1.07 | 1.44 | 1.34 |
| Aspen milled wood lignin (scientific, KTH) | 58.7 | 5.9 | 35.3 | 1.2 | 2.65 | 2.22 |
| Spruce milled wood lignin (scientific, KTH) | 59.2 | 6 | 34.6 | 1.21 | 2.75 | 2.28 |
| Spruce lignin (scientific, KTH) | 61.2 | 5.8 | 31.7 | 1.13 | 2.9 | 2.57 |
| Birch lignin (scientific, KTH) | 54.1 | 5.5 | 38 | 1.21 | 2.3 | 1.90 |
| Aspen lignin (scientific, KTH) | 59.2 | 5.7 | 33.2 | 1.15 | 1.15 | 1.82 |
| Lignin from EtOH plant, (scientific, Lund) | 55.2 | 6 | 38.6 | 1.3 | 2.47 | 1.90 |
| Lignin from EtOH plant, (scientific, College Bergen) | 63.3 | 4.7 | 31.33 | 0.88 | 2.38 | 2.69 |
| Lignin from EtOH plant, wa. (commercial, SEKAB) | 54.8 | 6.1 | 39.0 | 1.32 | 2.75 | 1.87 |
| Lignin from EtOH plant, e. (commercial, SEKAB) | 58.8 | 6.0 | 34.4 | 1.21 | 2.47 | 2.28 |

In the method of the present invention, the lignin material preferably comprises less than 50% by weight, more preferably less than 30% by weight and most preferably less than 15% by weight of cellulosic material.

The method of the present invention is preferably carried out in a single step. This means that the conversion of the lignin material to the liquid product is carried out in a single reaction, preferably without an interruption, e.g. an intermediate cooling step or separation step. Further, the method of the invention is preferably carried out in the absence of added gaseous $H_2$ and/or in the absence of any added catalyst, e.g. any metal-containing catalyst.

The treatment according to the invention may be carried out at elevated temperatures. The reaction temperature is preferably from 300-450° C., more preferably from 320-420° C., and most preferably from 350-400° C. The reaction is carried out as a slow pyrolysis process, wherein the heating of the reaction mixture occurs preferably with a rate of about 1-30° C./min. The reaction pressure is preferably 100-500 bar, more preferably from 100-250 bar. In another embodiment, the preferred pressure range is from 250-400 bar. The reaction time is preferably from 2 h to 100 h, more preferably from 10 h to 24 h. The weight ratio of lignin starting material to reaction medium is preferably from about 1:1 to about 1:12, more preferably from about 1:2 to about 1:10.

The reaction medium preferably comprises at least 10%, preferably 10 to 100% by weight of component (i), 0 to 60% by weight of component (ii), 0 to 50% by weight of component (iii) and 0 to 10% by weight of component (iv).

In a preferred embodiment component (ii) is present in an amount of from 2 to 60% by weight, more preferably of from 5 to 60% by weight.

Component (i) of the reaction medium comprises at least one $C_1$-$C_2$ carboxylic acid, e.g. formic acid and/or acetic acid and/or salts and/or esters thereof. Preferably, component (i) of the reaction medium comprises formic acid, and/or alkali salts, e.g. lithium, sodium and/or potassium salts, and/or esters, e.g. $C_1$-$C_3$ alcohol esters thereof. More particularly, the reaction medium comprises at least 20%, preferably at least 30%, more preferably at least 60% by weight formic acid, and/or alkali salts, e.g. lithium, sodium and/or potassium salts, and/or esters, e.g. $C_1$-$C_3$ alcohol esters thereof.

Formic acid may be produced by conventional means or by means of hydrothermal conversion of carbohydrate biomass at mild temperatures (13).

Further, the reaction medium optionally comprises as component (ii) at least one alcohol, e.g. an aliphatic alcohol, preferably at least one $C_1$-$C_5$ alcohol, more preferably at least one $C_1$-$C_3$ alcohol and/or water. The preferred $C_1$-$C_3$ alcohol may be selected from methanol, ethanol, n-propanol, isopropanol or mixtures thereof. The proportion of water in component (ii) is preferably less than 10% by volume. In a preferred embodiment component (ii) is a technical grade alcohol, e.g. an aliphatic alcohol, preferably at least one $C_{1-5}$ alcohol, more preferably at least one $C_{1-3}$ alcohol, comprising less than 10%, preferably less than 8%, even more preferably less than 5% by volume of water.

Further, the reaction medium optionally comprises as component (iii) an alkylating agent. The alkylating agent may be selected from dimethyl carbonate (DMC), tetramethylammonium hydroxide (TMAH) and/or combinations thereof.

Furthermore, the reaction medium may optionally comprise as component (iv) an inorganic salt. The inorganic salt may be selected from $NaCl$, $NaHCO_3$, $MgSO_4$, $FeSO_4$, $FeCl_3$, $FeBr_3$, $AlCl_3$, $AlBr_3$ and/or combinations thereof.

After the reaction has taken place, the reaction mixture preferably comprises two liquid phases, an organic phase containing the desired product and an aqueous phase. Further, small amounts of solid products, e.g. char and/or coke as well as gaseous reaction products may be present. The desired liquid organic product may be separated from the aqueous phase by conventional methods, e.g. in a separatory funnel or by decanting. If desired, the aqueous phase may be extracted with a hydrophobic organic solvent in order to obtain organic products present in the aqueous layer. Moreover, component (ii) which is present in both, the aqueous and the oily product phase, can be isolated and recycled, e.g. by destillation, in order to reduce the overall demand of these compounds.

The product obtainable by the method of the present invention comprises preferably, e.g. 50% by weight or more alkyl or polyalkyl phenols having a molecular weight in the range of 100-250 Da, more preferably in the range of 100-200 Da. Main product classes are aliphatic, both linear and branched hydrocarbons of up to ten carbon atoms and phenols with one or more $C_{1-3}$ substituents, but no methoxy groups are incorporated.

The amount of polyphenolic compounds in the product is less than 5% by weight (based on a total amount of product), more preferably less than 3% by weight and even more preferably less than 1% by weight.

The term "polyphenolic compounds" as used herein refers to aromatic compounds having at least two phenolic hydroxy groups per molecule. Examples for polyphenolic compounds include tannins, flavonoids and catechols.

The above described product composition shows markedly increased C/O and H/C molar ratios compared to the lignin source used (cf. Table 1), which result in an improved energy content relative to the starting material and which make them readily miscible with conventional fuels.

The elemental composition of the liquid product is:
60 to 85% C, preferably 70-85% C,
6.5 to 15% H, preferably 10-15% H,
2 to 25% O, preferably 2-7% O, and
0 to 1.0% S.

In another embodiment, the elemental composition of the liquid product is:
70 to 85% C, preferably 80-85% C,
7 to 15% H, preferably 10-15% H,
2 to 20% O, preferably 2-7% O, and
0 to 1.0% S.

The molar ratios of the main elements H, C and O are preferably:
H/C, 1.3 to 2.2, preferably 1.6-2.2,
H/O: 10 to 45, preferably 30-45, and
C/O: 5 to 30, preferably 20 to 30.

The yield of liquid product in the method of the present invention is preferably at least 80% by weight, more preferably at least 90% by weight, most preferably at least 95% by weight, based on the weight of the lignin starting material. The amount of solid product, e.g. char and/or coke, is preferably less than 20% by weight, more preferably less than 10% by weight, most preferably less than 5% by weight, based on the weight of the lignin starting material.

The aqueous phase obtained after the reaction may comprise from 0-60 wt.-%, preferably from 0-50 wt.-%, more preferably from 0-40 wt.-% and most preferably from 3-40 wt.-% of optionally substituted phenols based on the total amount of the aqueous phase.

The phenolic compounds may be readily extracted out of the aqueous phase by known solvents, such as dichloromethane or toluene, and can be added to the obtained product to increase yield.

If desired, combustible gases formed during the conversion, e.g. hydrogen carbon monoxide, methane, ethane and/or propane or mixtures thereof may be used for the heating in treatment step (b).

Furthermore, the obtained liquid product may be employed to substitute at least a part of the optional alcohol in component (ii), in order to significantly reduce the need of additional alcohols in the process.

The present invention further refers to a liquid product obtainable from lignin material wherein the elemental composition of the liquid product is:
60 to 85% C, preferably 70-85% C,
6.5 to 15% H, preferably 10-15% H,
2 to 25% O, preferably 2-7% O, and
0 to 1.0% S.

In another embodiment, the elemental composition of the liquid product is:
70 to 85% C, preferably 80-85% C,
7 to 15% H, preferably 10-15% H,
2 to 20% O, preferably 2-7% O, and
0 to 1.0% S.

The molar ratios of the main elements H, C and O are preferably:
H/C, 1.3 to 2.2, preferably 1.6-2.2,
H/O: 10 to 45, preferably 30-45, and
C/O: 5 to 30, preferably 20 to 30.

The lignin product obtainable according to the method of the present invention may be used as an addition to fuel, particularly for fuel for vehicles or as raw material for upgrading into petroleum-compatible fuels and other refining products, or as monomeric phenotic building blocks for the manufacture of organic polymers such as bio-plastics or resins.

Figure 1:
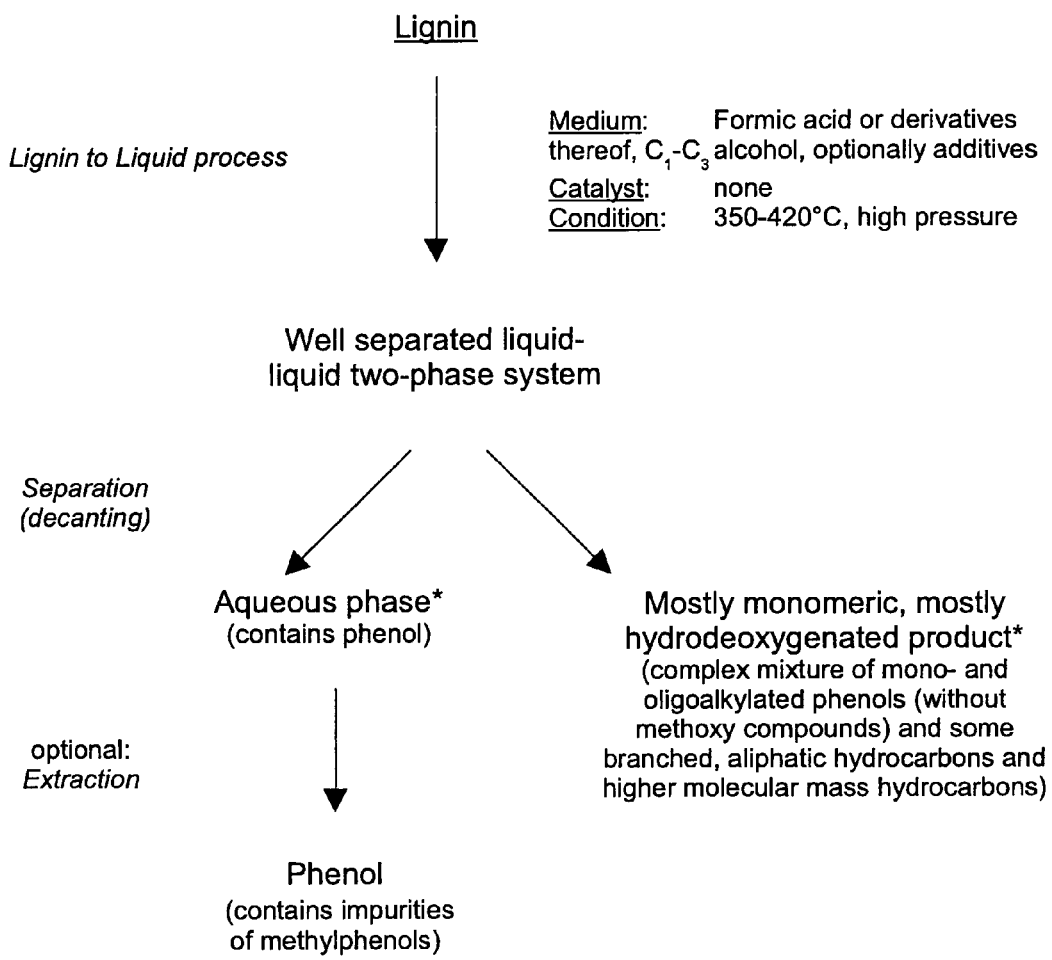
FIG. 1: Flowsheet of basic process steps

The present invention shall be explained further by the following example.

EXAMPLES

Experimental Part

Elemental Analysis. All samples were analyzed for their elemental composition in the CHNS mode with a Vario EL III machine using helium as the carrier gas. The amount of oxygen was calculated by difference.

GCMS Analysis. The liquid samples were analyzed on a GC-MSD (HP 5890-II with HP Auto 5890) and 25 m WCOT fused silica column (CP-Sil_8_CB) equipped with both FID and an HP5971 MSD detector and controlled by an HPChem laboratory data system. The run started at 50° C. for 2 min and then was heated at a rate of 6° C./min up to 320° C. The final temperature was held for 10 min. The injector temperature was 300° C.; the FID was at 350° C.; and the MSD had a temperature of 280° C. Compounds were identified using the Agilent MSD software and the NIST 05 library. The gases were analyzed on a GS (HP 6890 Series GC Plus) and a HP Plot Q-capillary equipped with an FID. The run started at 35° C. for 5 min and then was heated at a rate of 10° C./min up to 180° C. The final temperature was held for 22 min. The injector temperature was 150° C., and the FID was at 250° C.

Example 1

Lignin material (5 g) and a liquid reaction medium, a solvent mixture of component (i) and (ii) (15 ml formic acid and 20 ml ethanol) are placed in a high pressure reactor (75 ml non-stirred pressure vessel, Parr Instruments, Series 4740). After sealing the reactor is placed in an oven that can be electrically heated and might contain some fan to maintain better heat transfer by the hot air. Alternatively, the reactor can be placed in a bath of a hot medium (salt, sand etc.).

The reactor is heated from room temperature to 380° C. and maintained at that temperature for 14 hours. After that reaction time the reaction vessel is taken out of the heat source and allowed to cool to ambient temperature which might also be done more rapidly by immersing into or rinsing with cold water. After cooling the reactor is opened and gases are trapped.

A representative gas analysis showed that at the above stated conditions a mixture of ca. 8% methane, 36% ethane and 35% carbon dioxide is formed. In case of iso-propanol instead of ethanol the ratios are slight shifted and, more importantly, propane rather than ethane is produced. For example, the reaction of 6 g lignin, 12 ml formic acid and 18 ml iso-propanol for 17 h at 380° C. gives a gas composition of ca. 10% carbon monoxide, 15% methane, 30% carbon dioxide and 33% propane.

After opening the reactor the two phases are separated in a separatory funnel or by simple decanting. The crude reaction mixture contains a brownish top-layer that comprises the organic phase, the crude product-oil, and a clear, colourless aqueous phase that contains some phenol. To increase the yield of obtained organic products the aqueous layer can be extracted with any hydrophobic organic solvent, e.g. dichloromethane and/or toluene.

Rests of formic acid and in case of a traditional workup with extraction of the aqueous layer the organic solvents can be removed under reduced pressure. However, both phases show close to neutral pH (~6.5) indicating that formic acid is degraded at the reaction temperature used.

The low viscous, brownish oil is obtained with a yield of about 85% by weight and shows an elemental composition and molecular rations as follows: 77.83% C, 9.2% H, 12.2% O; H/C 1.41, H/O 11.99, C/O 8.50. The amount of formed coke is less than 5% (210 mg).

Different pyrolysis conditions provide bio-oils with properties indicated in Table 2:

TABLE 2

| SM [g] | comp. I [ml] | comp. II [ml] | comp. III [ml] | T [°C] | T [h] | C [%] | H [%] | O [%] | H/C mol. | H/O mol. | C/O mol. |
|---|---|---|---|---|---|---|---|---|---|---|---|
| 3.0[1] | 15 $HCO_2H$ | 20 EtOH | — | 400 | 16 | 76.8 | 13.5 | 8.9 | 1.9 | 20.0 | 10.0 |
| 1.0[2] | 4 $HCO_2H$ | 8 MeOH | — | 380 | 18 | 80.7 | 9.0 | 10.1 | 1.3 | 14.1 | 10.6 |
| 1.0[2] | 4 $HCO_2H$ | 8 MeOH | — | 380 | 18 | 80.7 | 9.0 | 10.1 | 1.3 | 14.1 | 10.6 |
| 0.7[2] | 6 $HCO_2H$ | 6 EtOH | — | 380 | 54 | 82.0 | 10.3 | 7.3 | 1.5 | 22.4 | 14.9 |
| 0.7[2] | 4 $HCO_2H$ | 8 $^{iso}$PrOH | — | 380 | 14 | 82.3 | 12.4 | 5.2 | 1.6 | 30.0 | 19.0 |
| 0.7[2] | 2 $HCO_2H$ | 10 EtOH | 2DMC | 380 | 32 | 83.0 | 11.0 | 5.6 | 1.5 | 30.7 | 20.0 |
| 1.0[2] | 6 $HCO_2H$ | 6 EtOH | — | 380 | 14 | 82.0 | 10.3 | 7.3 | 1.5 | 22.4 | 14.9 |
| 0.7[2] | 6 $HCO_2H$ | — | 2DMC | 380 | 14 | 69.96 | 7.05 | 22.30 | 1.2 | 5.0 | 4.2 |
| 2.0[2] | 3 $HCO_2H$ | 2.3 isoPrOH 2.3 EtOH | — | 380 | 16 | 81.47 | 8.93 | 9.32 | 1.3 | 15.2 | 11.6 |
| 1.25[2] | 3 $HCO_2H$ | 3.0 isoPrOH 2.4 EtOH | — | 380 | 10.5 | 79.83 | 11.77 | 7.29 | 1.8 | 25.6 | 14.5 |
| 3.75[1] | 9 $HCO_2H$ | 9.3 isoPrOH 7.1 EtOH | — | 380 | 16 | 73.76 | 10.24 | 16.09 | 1.7 | 10.1 | 6.09 |

[1] 75 ml non-stirred pressure vessel from Parr Instruments, Series 4740.
[2] 25 ml non-stirred pressure vessel from Parr Instruments, Series 4742.

The molecular composition of the organic liquids depends on the reaction conditions that are used, especially regarding the proportion of hydrocarbon products relative to phenols.

Example 2

Lignin material (5 g, Aspen lignin, scientific KTH) and a liquid reaction medium, a solvent mixture of component (i) and (ii) (8 ml formic acid, 24 ml ethanol and 9 ml 2-propanol) are placed in a high pressure reactor (75 ml non-stirred pressure vessel, Parr Instruments, Series 4740). After sealing the reactor is placed in an oven that can be electrically heated and might contain some fan to maintain better heat transfer by the hot air. Alternatively, the reactor can be placed in a bath of a hot medium (salt, sand etc.).

The reactor is heated from room temperature to 380° C. and maintained at that temperature for 19 hours. After that reaction time the reaction vessel is taken out of the heat source and allowed to cool to ambient temperature which might also be done more rapidly by immersing into or rinsing with cold water. After cooling the reactor is opened and gases are trapped.

Figure 2:
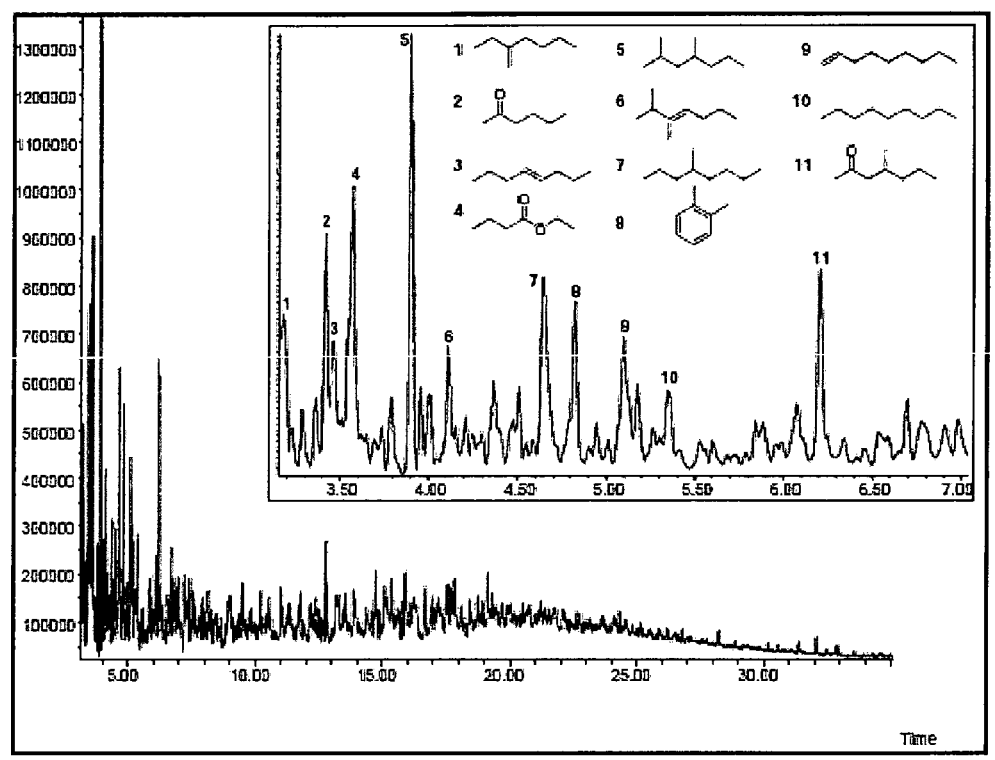
FIG. 2: GC/MS chromatogram of Example 2 with predominantly aliphatic hydrocarbons of the $C_6$-$C_{10}$ backbone and almost no phenols.

FIG. 2 shows a GC/MS chromatogram of the obtained oil where aliphatic hydrocarbons and esters are the most abundant compounds within the volatility range covered by the analysis. 2,4-dimethyl-heptane is the most abundant product. This composition would be suitable for further refining to motor fuels.

Example 3

Lignin material (6 g, enzymatic hydrolysis lignin, commercial, SEKAB) and a liquid reaction medium, a solvent mixture of component (i) and an inert, lipophilic organic solvent to maintain the high pressure without any potential to react with the other reaction components present (6 ml formic acid and 13 ml heptan) are placed in a high pressure reactor (75 ml non-stirred pressure vessel, Parr instruments, Series 4740). After sealing the reactor is placed in an oven that can be electrically heated and might contain some fan to maintain better heat transfer by the hot air. Alternatively, the reactor can be placed in a bath of a hot medium (salt, sand etc.).

The reactor is heated from room temperature to 380° C. and maintained at that temperature for 15 hours. After that reaction time the reaction vessel is taken out of the heat source and allowed to cool to ambient temperature which might also be done more rapidly by immersing into or rinsing with cold water. After cooling the reactor is opened and gases are trapped.

Figure 3:
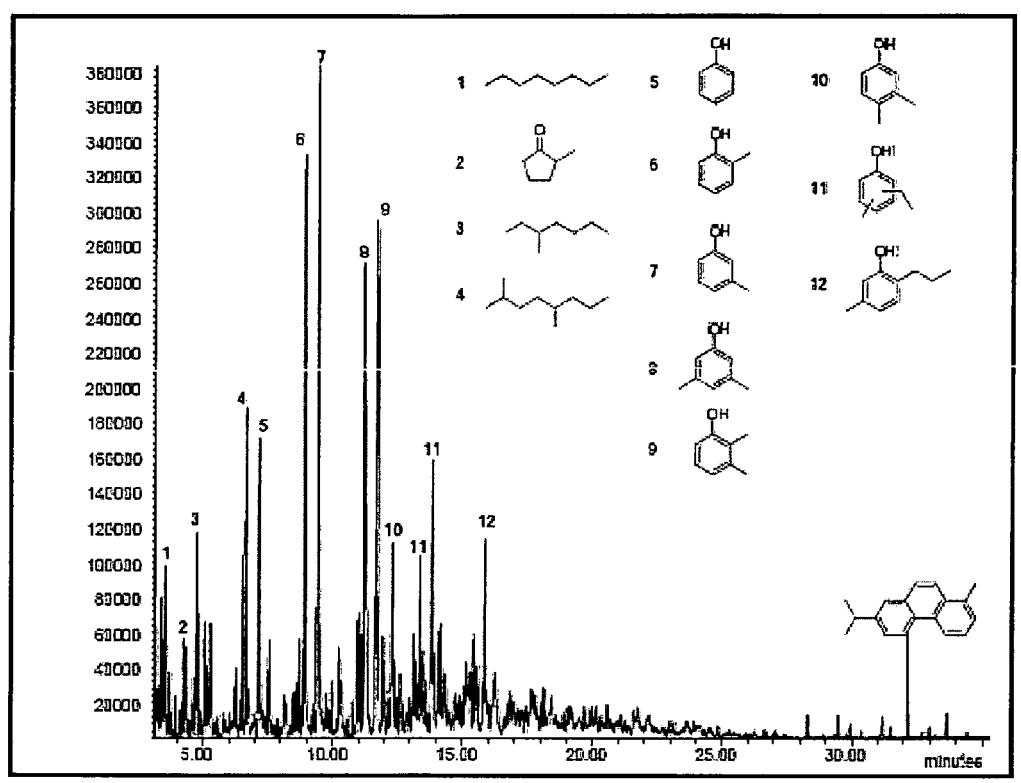
FIG. 3: GC/MS chromatogram of Example 3 with substituted phenols forming the major compound class qualitatively and quantitatively.

FIG. 3 shows the product spectrum dominated by monomeric phenols with mostly methyl group substituents. Monomethyl phenols and dimethyl phenols are among the most abundant products. This product composition would be a promising starting material for the production of phenols.

Example 4

Lignin material (6 g, strong acid hydrolysis lignin, scientific, College of Bergen) and a liquid reaction medium, a solvent mixture of component (i) and (ii) (15 ml formic acid and 15 ml 2-propanol) are placed in a high pressure reactor (75 ml non-stirred pressure vessel, Parr Instruments, Series 4740). After sealing the reactor is placed in an oven that can be electrically heated and might contain some fan to maintain better heat transfer by the hot air. Alternatively, the reactor can be placed in a bath of a hot medium (salt, sand etc.).

The reactor is heated from room temperature to 380° C. and maintained at that temperature for 15 hours. After that reaction time the reaction vessel is taken out of the heat source and allowed to cool to ambient temperature which might also be done more rapidly by immersing into or rinsing with cold water. After cooling the reactor is opened and gases are trapped.

Figure 4:
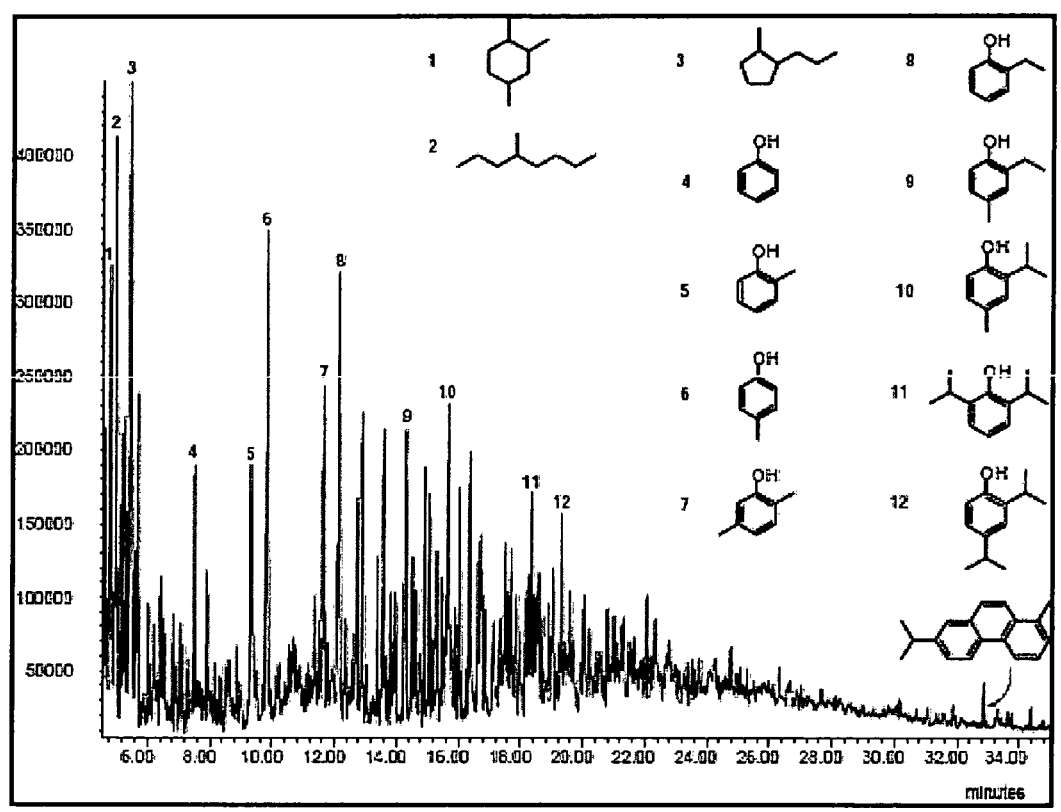
FIG. 4: GC/MS chromatogram of Example 4 with both aliphatics and phenols being almost equally abundant. Separation of these fractions can conveniently be achieved by column chromatography or destillation.

In FIG. 4 the obtained product spectrum is depicted showing a mixture of the two major compound classes of Examples 2 and 3. The aliphatics are the predominating compounds quantitatively, but the phenolic domain at retention times over around 8 minutes, a complex mixture of a very large number of different components, is almost equally abundant. Interesting with respect to applications is the option for separating the two fractions. Aliphatics and phenols could be separated very conveniently by a short plug silicon column chromatography with a gradient solvent system of e.g. cyclohexane (elutes aliphatics) and 1:1 cyclohexane/ethyl acetate (elutes phenols).

Product Composition

The formed bio-oils that are derived from the biopolymer lignin (up to 5000 Da) show a certain mass distribution. By means of MALDI-Tof and ESI-MS the largest masses appear to be in the range of less than 700 Da with the majority being around 200-300 Da. The more detailed GC/MS analysis confirms that these masses are not the predominating fraction of the product. Monomeric lignin units of alkyl or polyalkyl phenols and aliphatics (100-250 Da, more preferably 100-200 Da) make up the major product fraction. To a small degree Fischer-Tropsch-type of products could also be determined, but these also represent a minor product fraction.

The presence of alkyl phenols is of particular value as these compounds possess high octane numbers and are therefore most interesting as fuel blending components.

LIST OF REFERENCES

1. J. Goldemberg, Science 315, 808 (2007).
2. F. Demirbas, Energy Sources 28, 1181 (2006).
3. G. W. Huber, S. Iborra, A. Corma, Chem. Rev. 106, 4044 (2006).
4. C. N. Hamelincka, A. P. C. Faaijb, Energy Policy 34, 3268 (2006).
5. S. Fernando, S. Adhikari, C. Chandrapal, N. Murali, Energy & Fuels 20, 1727 (2006).
6. A. J. Ragauskas, C. K. Williams, B. H. Davison, G. Britovsek, J. Cairney, C. A. Eckert, W. J. Frederick Jr., J. P. Hallett, D. J. Leak, C. L. Liotta, J. R. Mielenz, R. Murphy, R. Templer, T. Tschaplinski, Science 311, 484 (2006).
7. D. Mohan, C. U. Jr. Pittman, P. H. Steele, Energy & Fuels 20, 848 (2006).
8. T. Barth, Organic Geochemistry 12, 1495 (1999).
9. A. V. Bridgwater, Chem. Ind. J. 91, 87 (2003).
10. A. Oasmaa, R. Aln, D. Meier, Biores. Technol. 45, 189 (1993).
11. W. W. Zmierczak, J. D. Miller, WO 2006/119357.
12. Titov, A. WO 03/074632.
13. F. Jin, J. Yun, G. Li, A. Kishita, K. Tohji, H. Enemoto, Green Chem. 10, 612 (2008)]

The invention claimed is:

1. A method of converting a lignin material into a liquid product, comprising the steps:
    (a) providing a lignin starting material,
    (b) subjecting said starting material to a treatment in a reaction medium under elevated pressure, wherein the reaction temperature is from 300-450° C. and the reaction pressure is from 100-500 bar, comprising:
        (i) at least one C1-C2 carboxylic acid, and/or salts and/or esters thereof,
        (ii) optionally at least one alcohol and/or water,
        (iii) optionally an alkylating agent, and
        (iv) optionally an inorganic salt,
    wherein said starting material is converted to a liquid product, and (c) obtaining the liquid product from the reaction medium.

2. The method of claim 1, wherein the lignin material comprises less than 50% by weight of cellulosic material.

3. The method of claim 1, which is carried out in a single step.

4. The method of claim 1, which is carried out in the absence of added gaseous H2 and/or in the absence of any added catalyst.

5. The method of claim 1, wherein the reaction temperature is from 320-420° C.

6. The method of claim 1, wherein the reaction mixture is heated with a rate of about 1 to 30° C./min.

7. The method of claim 1, wherein the reaction pressure is from 100 to 500 bar.

8. The method of claim 1, wherein the reaction time is from 2 h to 24 h.

9. The method of claim 1, wherein the weight ratio of lignin material to reaction medium is from about 1:1 to about 1:12.

10. The method of claim 1, wherein the reaction medium comprises at least 10% by weight of component (i), 0 to 60% by weight of component (ii), 0 to 50% by weight of component (iii) and 0 to 10% by weight of component (iv).

11. The method of claim 1, wherein component (i) of the reaction medium comprises formic acid, and/or alkali salts, and/or esters.

12. The method of claim 1, wherein the reaction medium comprises at least 20%, by weight formic acid, and/or alkali salts, and/or esters.

13. The method of claim 1, wherein the alkylating agent comprises dimethyl carbonate (DMC), tetramethylammonium hydroxide (TMAH) and/or combinations thereof.

14. The method of claim 1, wherein the inorganic salt is selected from NaCl, NaHCO3, MgSO4, FeSO4, FeCl3, FeBr3, AlCl3, AlBr3 and/or combinations thereof.

15. The method of claim 1, wherein the elemental composition of the liquid product is:
    60 to 85% C,
    6.5 to 15% H,
    2 to 25% O, and
    0 to 1.0% S.

16. The method of claim 1, wherein the liquid product has a molar ratio:
    H/C, 1.3 to 2.2,
    H/O: 10 to 45, and
    C/O: 5 to 30.

17. The method of claim 1, wherein the yield of liquid product is at least 80% by weight based on the weight of the lignin starting material.

18. The method of claim 1, wherein the amount of solid product, is less than 20% by weight based on the weight of the lignin starting material.

19. The method of claim 1, wherein gases formed during the conversion are used for heating in treatment step (b).

20. A liquid product obtainable from lignin material according to the method of claim 1 wherein the elemental composition of the liquid product is:
    60 to 85% C,
    6.5 to 15 H,
    2 to 25% O, and
    0 to 1.0% S.

21. The liquid product of claim 20,
    wherein the liquid product has a molar ratio:
    H/C, 1.3 to 2.2,
    H/O: 10 to 45, and
    C/O: 5 to 30.

22. A method of using the liquid product of claim 20 as an addition to fuel, particularly to fuel for vehicles or as raw material for upgrading into petroleum-compatible fuels and other refining products or as monomeric building blocks for the manufacture of organic polymers, comprising adding said liquid product to said fuel.

23. The method of claim 1, wherein the lignin material comprises less than 30% by weight of cellulosic material.

24. The method of claim 1, wherein the reaction pressure is from 100-250 bar.

25. The method of claim 1, wherein the reaction medium comprises 10 to 100% by weight of component (i), 0 to 60% by weight of component (ii), 0 to 50% by weight of component (iii) and 0 to 10% by weight of component (iv).

26. The method of claim 1, wherein the elemental composition of the liquid product is:
    70 to 85% C,
    10 to 15% H,
    2 to 7% O, and
    0 to 1.0% S.

27. The method of claim 1, wherein the liquid product has a molar ratio:
  H/C, 1.6 to 2.2
  H/O: 30 to 45, and
  C/O: 20 to 30.

28. The method of claim 1, wherein the yield of liquid product is at least 90% by weight based on the weight of the lignin starting material.

29. The method of claim 1, wherein the amount of solid product is less than 10% by weight based on the weight of the ligin starting material.

30. A liquid product obtainable from lignin material according to the method of claim 1 wherein the elemental composition of the liquid product is:
  70 to 85% C,
  10 to 15% H,
  2 to 7% O, and
  0 to 1.0% S.

31. The liquid product of claim 20, wherein the liquid product has a molar ratio:
  H/C, 1.6 to 2.2,
  H/O: 30 to 45, and
  C/O: 20 to 30.

32. The method of claim 11, wherein the alkali salts are lithium, sodium, or potassium salts.

33. The method of claim 11, wherein the esters are C1-C3 alcohol esters.

34. The method of claim 12, wherein the reaction medium comprises 60% by weight formic acid.

35. The method of claim 12, wherein the alkali salts are lithium, sodium, or potassium salts.

36. The method of claim 12, wherein the esters are C1-C3 alcohol esters.

37. The method of claim 18, wherein the solid product is char or coke.

38. The method of claim 29, wherein the solid product is char or coke.

* * * * *